United States Patent

Conners

[11] Patent Number: 5,258,009
[45] Date of Patent: Nov. 2, 1993

[54] MALLEABLE, BIOABSORBABLE, PLASTIC STAPLE HAVING A KNOTTED CONFIGURATION; AND METHOD AND APPARATUS FOR DEFORMING SUCH STAPLE

[75] Inventor: John A. Conners, Fairfield, Conn.

[73] Assignee: American Cyanamid Company, Stamford, Conn.

[21] Appl. No.: 906,937

[22] Filed: Jun. 30, 1992

[51] Int. Cl.$^5$ ............................................ A61B 17/00
[52] U.S. Cl. .................... 606/219; 411/457; 411/904; 411/920
[58] Field of Search ........... 606/219; 411/457, 904, 411/920

[56] References Cited
U.S. PATENT DOCUMENTS

| | | | |
|---|---|---|---|
| 4,262,836 | 4/1981 | Hirose | 227/110 |
| 4,526,174 | 7/1985 | Froehlich | 606/219 |
| 4,532,927 | 8/1985 | Miksza, Jr. | 606/220 |
| 4,671,280 | 6/1987 | Dorband et al. | 606/220 |
| 5,080,665 | 1/1992 | Jarrett et al. | 606/219 |

*Primary Examiner*—Max Hindenburg
*Assistant Examiner*—Gary Jackson
*Attorney, Agent, or Firm*—Charles F. Costello, Jr.

[57] ABSTRACT

A malleable, bioabsorbable polymeric staple includes a back span with two legs depending perpendicularly therefrom that are deformed along an arcuate path toward each other initially and then upwardly toward the back span such that end points on each leg extend through a gap formed between an underside of the back span and a bend in an opposite leg. A surgical staple-deforming anvil for deforming the staples has a staple-receiving face formed with a pair of guiding path depressions each having an entry end lying on a longitudinal axis parallel to the back span of the staple, and an exit end. The guiding paths are arcuately shaped and form a groove curving and crossing each other approximately at the longitudinal axis. Accordingly, the legs of a staple driven toward the anvil and received in the guiding paths are initially bent toward each other and then steered upwardly and along the horizontally curved path toward the gap formed between the back span and the bend in the opposite leg.

4 Claims, 3 Drawing Sheets

MALLEABLE, BIOABSORBABLE, PLASTIC STAPLE HAVING A KNOTTED CONFIGURATION; AND METHOD AND APPARATUS FOR DEFORMING SUCH STAPLE

BACKGROUND OF THE INVENTION

1. Field of the Invention

The present invention relates to surgical staples and to a method and an apparatus, particularly an anvil for a surgical stapling device, used to deform such staples to secure adjacent layers of tissue together. More specifically, this invention relates to the configuration of malleable, bioabsorbable, plastic or polymeric staples for suturing body organs and tissue, and to a precision-formed anvil for deforming the staples into that suturing configuration.

2. Description of the Prior Art

Historically, suturing of a surgical or other wound in organs and tissue has been done by hand. Conventional hand suturing techniques require a high degree of surgical skill. However, expertise in such techniques can vary widely from surgeon to surgeon, thereby resulting in widely varying quality in performance of the concluding steps of an operative procedure. In addition, even very skillful surgeons require a considerable amount of time to suture even relatively small wounds. Therefore, it is possible that an undesirable amount of blood may be lost during the suturing operation.

Accordingly, there has been an increasing tendency in recent years to use surgical staples to suture body organs and tissue after a medical procedure. Surgical staples have been particularly effective in suturing body organs and tissue such as the lung, as well as the esophagus, the stomach, the duodenum, and other body organs in the intestinal tract.

The advent of surgical stapling has provided several marked advantages over known hand suturing techniques. First, since one or more rows of surgical staples are inserted into tissue using a specially adapted instrument that is simply actuated, near uniformity of the closure from one surgeon to the next results. In addition, all staples in the closure are usually inserted simultaneously or in rapid sequence across the entire wound. Therefore, the closure is made very quickly to minimize loss of blood.

Surgical staples are usually mechanically inserted into tissue with surgical stapling instruments such as those known as anastomosis devices, including gastrointestinal anastomosis devices and transverse anastomosis devices. In such devices, the staples are loaded in one or more elongated rows into a magazine or cartridge. The magazine is then mounted in the device, which includes a mechanism for pushing, or driving, the staples from the magazine through two or more sections of tissue toward a deforming anvil. At the conclusion of the driving operation, the legs of each staple are conventionally clamped or bent, by engagement with the anvil, to a closed configuration to complete the suture and join the tissue sections together.

Gastrointestinal anastomosis-type devices drive and bend the staples aligned in a row one after the other in rapid sequence. Transverse anastomosis-type devices drive and bend all staples in a row simultaneously.

One type of conventional staple 10, shown in FIG. 1, used with both gastrointestinal anastomosis and transverse anastomosis-type surgical stapling devices is made of a metal, like stainless steel or titanium, that is substantially inert in the body. The undeformed staple 10, or staple blank, is generally U-shaped and includes a back span 12 and two legs 14 depending perpendicularly from the back span in parallel to one another. Each leg 14 has a sharp chiseled end point 16 for cleanly piercing body organs or tissue. The metal staple blank is bent by having the legs engage and follow a conventional anvil to form a B-shaped closed staple 18 as shown in FIG. 2.

The anvil used to bend metal surgical staples is also formed of a hardened metal and includes a staplebending face having a pair of coined or punched pockets located to oppose each staple in the magazine of the stapling device. The pockets are ordinarily elongated arcuate depressions, co-linearly arranged in parallel to the back span of a corresponding staple held in the magazine. Thus the anvil closely resembles the anvil of a conventional paper stapler.

When the staples 10 are driven from the magazine toward the anvil, the staple legs 14 each engage one pocket so that both legs are bent toward each other initially and thereafter upwardly toward the back span 12. Thus, as shown in FIG. 2, the end points 16 may come to rest against the underside of the back span 12.

Although metal staples inserted in the manner described above provide an effective and relatively simple means of suturing, one significant disadvantage is that they remain in the patient's body permanently. While generally not injurious to the body they may nevertheless interfere with post-operative X-ray or other diagnostic imaging of the patient.

This disadvantage can be overcome by using bioabsorbable polymeric staples that are degradable in the body after a short period of time. However, conventional polymeric staples are not malleable and thus cannot be easily bent into the B-shaped configuration shown in FIG. 2, to complete a suture. Therefore, as shown in FIG. 3, such conventional bioabsorbable staples instead are made in two parts, namely a U-shaped polymeric staple body 20, the legs 22 of which are joined by a polymeric bar-like closure 24. The closure has two end point-receiving holes 26 that fit over the end points of the staple body 20 after they have pierced the tissue to be sutured. The staple body 20 and closure 24 are then forced toward each other to complete the suture.

While this two-part staple will dissolve in the body and, therefore, does not interfere with post-operative procedures, it has the drawback of requiring a part in addition to the basic staple blank and thus requires a more complicated mechanical stapling device for properly aligning the two parts and driving them together.

More recently, the assignee of the subject invention has made a breakthrough in the bioabsorbable staple field. Specifically as described in U.S. Pat. application Ser. Nos. 07/548,802, now U.S. Pat. No. 5,080,665, and 07/548,803, both filed Jul. 6, 1990, and U.S. Pat. application Ser. No. 07/799,521, filed Nov. 27, 1991, which are incorporated herein by reference, bioabsorbable or partially bioabsorbable surgical staples have been developed using polymeric materials. (Hereinafter the term "bioabsorbable" will be used generically to describe surgical staples of the type described in both of the applications mentioned above.) These staples retain all of the beneficial attributes of known bioabsorbable staples, but in addition are malleable or plastically deformable like metal staples. That is, these staples may be bent into complex shapes that are then retained. Therefore, they may be made of a single piece, not requiring independent staple body and closure parts.

Nevertheless, it has been found that if these new bioabsorbable staples are bent in the same way as are conventional metal staples, as shown in FIG. 2, so that the chiseled end points of the staple legs hit the back span, the points may crush or break.

Therefore, improvements in surgical staples and devices for inserting them, taking advantage of the attributes of the new polymeric materials described above, are desirable.

SUMMARY OF THE INVENTION

Accordingly, it is a principle object of the present invention to enhance the benefits obtained by using malleable, bioabsorbable, polymeric staples in surgical stapling techniques.

It is a further object of the present invention to provide a malleable, bioabsorbable, polymeric staple deformed into a precise shape that securely joins tissue sections together with minimal tissue injury and damage to the staple itself.

It is another object of the present invention to provide a malleable, bioabsorbable, polymeric staple deformed into a knotted configuration to better secure the stapled tissue.

It is yet another object of the present invention to provide a malleable, bioabsorbable, polymeric staple having a variable closing force for securing the stapled tissue.

It is another object of the present invention to provide a high precision anvil for surgical stapling devices that will precisely and uniformly deform malleable, bioabsorbable, polymeric staples, as well as other staples, into a desired configuration.

It is yet another object of the present invention to provide a method for deforming the malleable, bioabsorbable, polymeric staples into the desired shape.

It is still another object of the present invention to provide a unique anvil that takes advantage of the beneficial properties of malleable, bioabsorbable, polymeric staples of the type described above to in turn provide an improved surgical stapling device.

These and other objects are achieved by the malleable, bioabsorbable, polymeric surgical staple of the present invention, which in a preferred embodiment comprises a back span, and first and second legs extending in a first direction from opposite ends of the back span, with each of the first and second legs terminating in an end point. Each leg includes a bend and a curved portion extending across a vertical plane extending in the first direction and through the back span, with the curved portions of each respective leg crossing with each other.

In accordance with another aspect, a preferred method is disclosed for deforming a malleable, bioabsorbable, polymeric surgical staple having a back span, first and second legs extending in a first direction from opposite ends of the back span and substantially perpendicularly thereto in an undeformed state, the first and second legs each terminating in an end point. The method comprises the steps of initially deforming the first and second legs inwardly toward each other to form a bend in each leg, with each leg having a straight portion between the back span and the bend, and thereafter deforming in each leg a curved portion leading from the bend and extending to the end point into an arcuate shape extending across a vertical plane defined in the first direction and passing through the back span, with the curved portions of each leg crossing each other.

In accordance with yet another aspect, a preferred embodiment of the invention is a surgical stapling device anvil for deforming a malleable surgical staple having a back span, and first and second legs extending in one direction from opposite ends of the back span and substantially perpendicularly thereto in an undeformed state. The anvil comprises a supporting body having a longitudinal axis and including a staple-receiving face in a horizontal plane, first and second pocket depressions each beginning with an entry end located at the staple-receiving face, continuing to a depressed portion within the body below the staple-receiving face, and terminating in an exit end at the staple-receiving face. The first and second pocket depressions each have an arcuate portion and extend in non-collinear relation with the entry end of each located substantially on the longitudinal axis, and the exit end of each is located on a side of the longitudinal axis opposite the side on which the exit end of the other pocket depression is located, with the arcuate portions curving along the horizontal plane to form a bend and crossing each other approximately at the longitudinal axis. The first and second legs of a staple driven toward the anvil and received in the entry ends of the respective first and second pocket depressions are guided to the exit ends thereof to be deformed toward the back span and formed such that distal ends of the first and second legs extend between the bend in the opposite leg and the back span.

It will be appreciated, of course, that the surgical stapling device anvil configured in accordance with the present invention may be used with surgical staples of any material. However, because it is specifically designed for use with malleable, bioabsorbable, polymeric staples that are non-metallic, it may be made of plastic materials that are less expensive and in which the high precision pocket-like depressions may be more easily formed than known hardened metal anvils.

These and other objects, aspects, features, and advantages of the present invention will become apparent from the following detailed description of the preferred embodiments taken in conjunction with the drawings.

DETAILED DESCRIPTION OF THE PREFERRED EMBODIMENTS

As noted above, surgical staples in accordance with the present invention are made of an inventive polymeric or plastic material disclosed in detail in copending U.S. Pat. application Ser. Nos. 07/548,802, now U.S. Pat. No. 5,080,665, 07/548,803, and 07/799,521, which are incorporated herein by reference. Because they are made of this unique material, these staples are plastically deformable or malleable as well as bioabsorbable. The present invention takes advantage of these unique properties to provide a surgical staple having an improved deformed configuration, a method of deforming the staple to that configuration, and a surgical stapling device anvil, the use of which results in that configuration. Of course other bioabsorbable or partially bioabsorbable malleable polymeric staples later developed may be adapted to the present invention.

Figure 4:
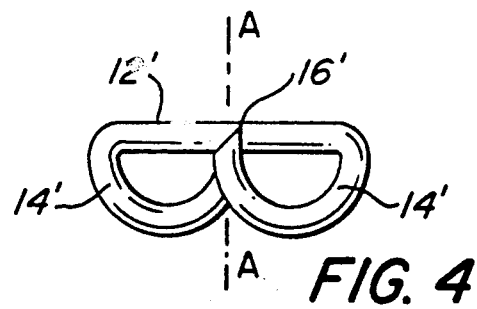
FIG. 4 is a front elevational view of a malleable, bioabsorbable, polymeric staple in its deformed state in accordance with the invention disclosed in U.S. Pat. application Ser. No. 07/785,295, filed Oct. 30, 1991, which is assigned to the assignee of the present invention.
Figure 5:
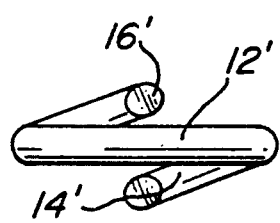
FIG. 5 is a top plan view of the staple shown in FIG. 4.

An improved malleable, bioabsorbable, plastic staple, and method and apparatus for deforming such staple, are the subject of U.S. Pat. application Ser. No. 07/785,295, filed Oct. 30, 1991, and assigned to the assignee of the subject application. That application is also incorporated herein by reference. As shown in FIGS. 4 and 5, that application discloses a plastic staple with legs 14' that are initially bent toward each other and then steered upwardly toward opposite sides of back span 12' to form a so called offset B-shape. This configuration protects the brittle end points from hitting the underside of the back span. The present invention is directed to an alternative plastic staple configuration and to the method of achieving it.

Figure 1:
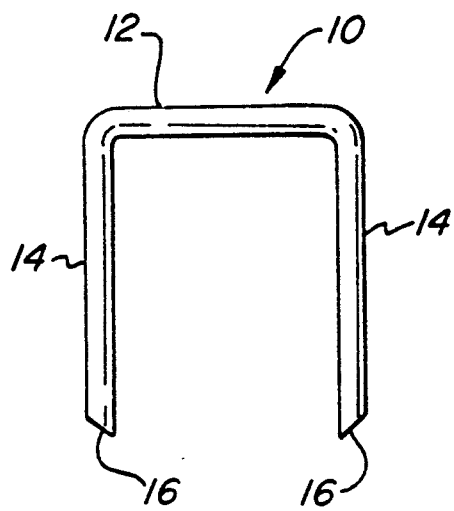
FIG. 1 a front elevational view of a conventional metal staple bank made, for example, of stainless steel or titanium.
Figure 2:
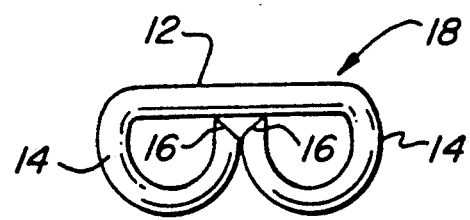
FIG. 2 is a front elevational view of a conventional staple in a deformed configuration.
Figure 3:
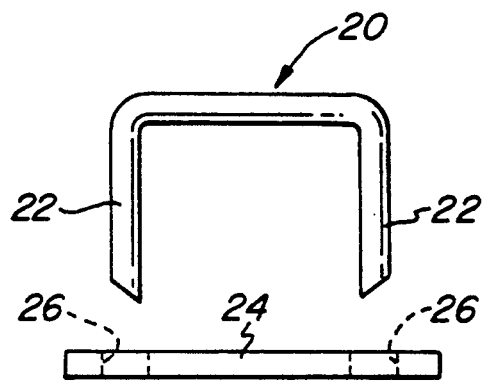
FIG. 3 is a front elevational view of a conventional two-piece bioabsorbable polymeric staple.
Figure 6:
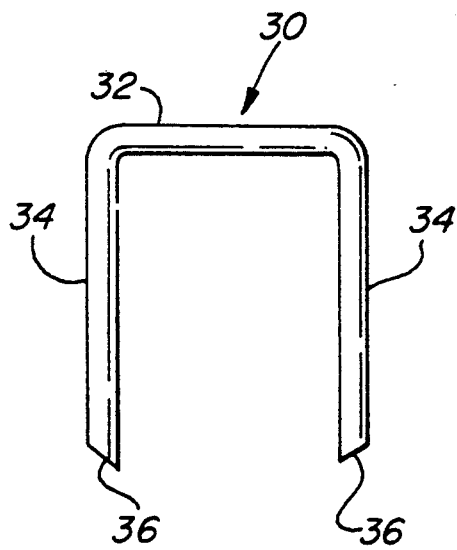
FIG. 6 is a front elevational view of a malleable, bioabsorbable, polymeric staple, which is not yet deformed, in accordance with the present invention.

More particularly, in its undeformed state shown in FIG. 6, the surgical staple or staple blank 30 in accordance with the present invention is generally U-shaped as are conventional staples shown in FIG. 1. Thus the improved staple 30 includes a back span 32, two legs 34, and an end point 36 formed at the extreme of each leg 34. The end points are sharply chiseled to cleanly pierce the body organs or tissue to be sutured.

Figure 7:
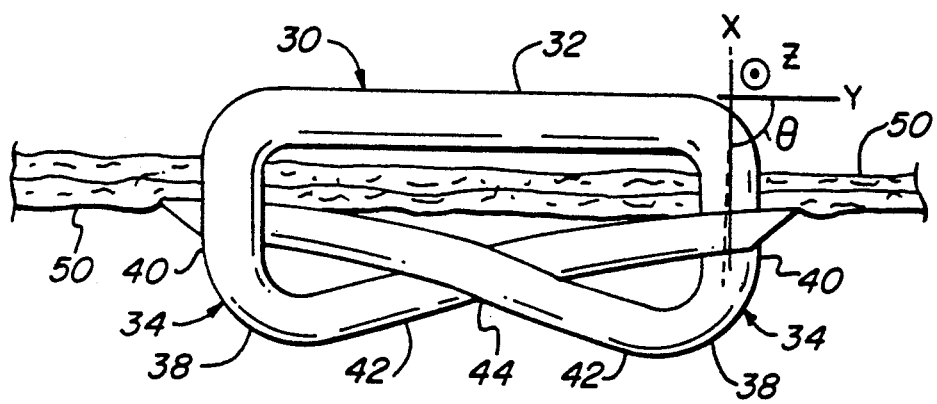
FIG. 7 is a cross-sectional side view of a malleable, bioabsorbable, polymeric staple gripping two layers of tissue in its deformed state in accordance with the present invention.
Figure 8:
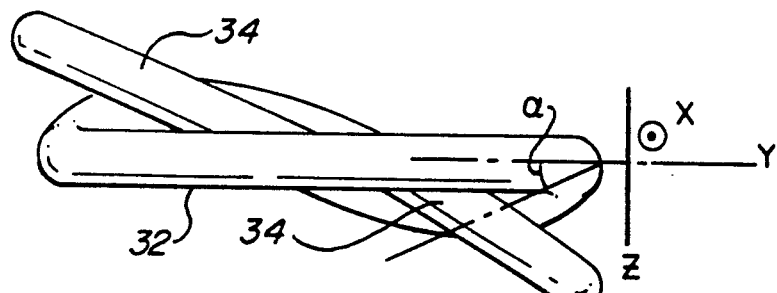
FIG. 8 is a top plan view of the staple deformed in the shape shown in FIG. 7 in accordance with the present invention.

FIGS. 7 and 8 show the plastic staple 30 in accordance with the present invention in its deformed state. The staple is shown as having pierced two layers of tissue 50 to be sutured. Each leg 34 is similarly deformed to include a bend 38, with a straight first portion 40 between the bend and the back span 32 and a curved second portion 42 at a distal end of the bend.

In deforming the staple with an anvil, which will be describe below, first bend 38 is formed at an intermediate location on each leg. As shown in FIG. 7, the straight first portion extends substantially perpendicularly from the back span in a vertical, or x-axis, direction. Actually, each leg is preferably bent slightly inwardly when the bend is formed and thus forms an angle $\theta$ with the horizonal y-axis of slightly more than 90° in the x-y plane. After the bend is formed, the curved second portions are guided in the anvil toward each other and then upwardly toward the back span along a path which is arcuately curved in the horizontal plane, that is, the y-z plane in FIG. 7.

As best seen in FIG. 8, each curved second portion extends from the bend at an angle $\alpha$ of approximately 20° from the vertical x-y plane and curves back around and under the back span, thus crossing the vertical x-y plane defined by back span 32 and the first portions of legs 34. Since each leg is bent in the same manner, the legs cross the curved second portions to form a knot 44, and the end points extend through a gap between the underside of the back span and tissue layers and the bend of the opposite leg. With legs 34 deformed in this manner, the staple loosely resembles a pretzel and the configuration can be referred to as a "pretzel" or "knotted" design. One significant advantage of this design over conventionally deformed staples is that the end points of each leg are sandwiched in the gap between the back span and the bend of the opposite leg, and the curved configuration of the legs makes it difficult, if not impossible, for the staple to relax so as to slide out from the gap. Thus, the staple remains in its deformed state and a secure suture in the tissue is maintained.

Another advantage of the pretzel staple design is that, with reference to FIG. 7, the end points of the legs do not pierce the tissue a second time from the underside. Rather, the gentle upward slope of the anvil deforms the second curved portions of the legs at such a slight angle that the legs can actually compress the tissue with a force against the back span. Moreover, this compression, or closing, force can be regulated by varying the stroke of the stapler against the staple in the anvil and thus the length of the straight first portion.

Figure 9:
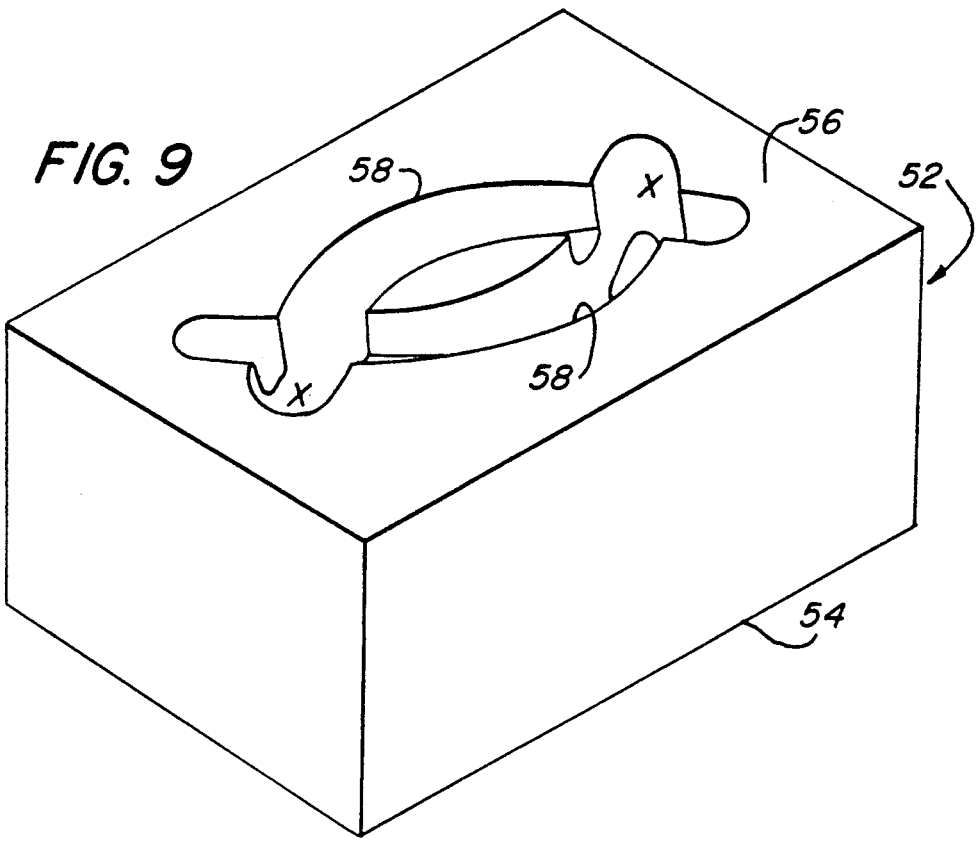
FIG. 9 is a schematic perspective view of a surgical stapling device anvil formed in accordance with an embodiment of the invention.
Figure 10:
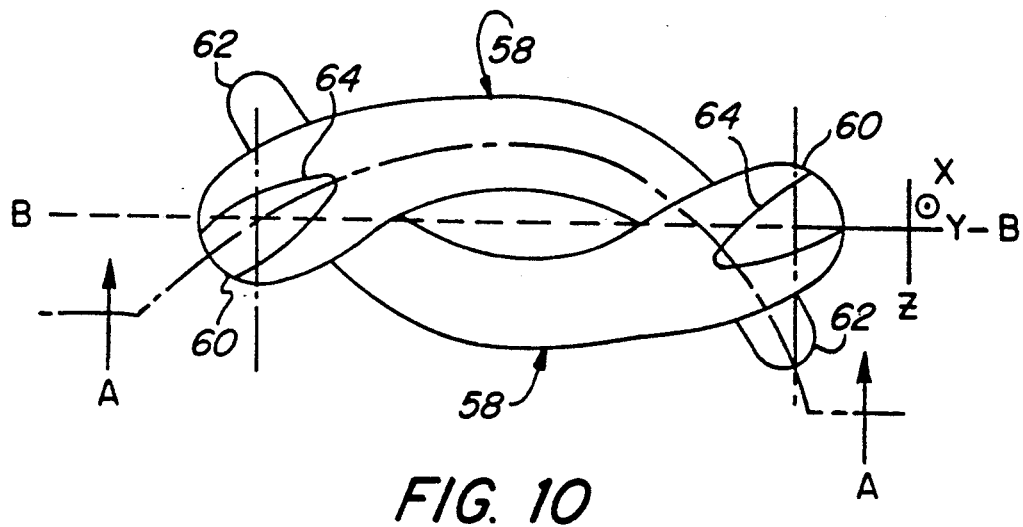
FIG. 10 is a schematic top plan view of the surgical stapling device anvil shown in FIG. 9.
Figure 11:
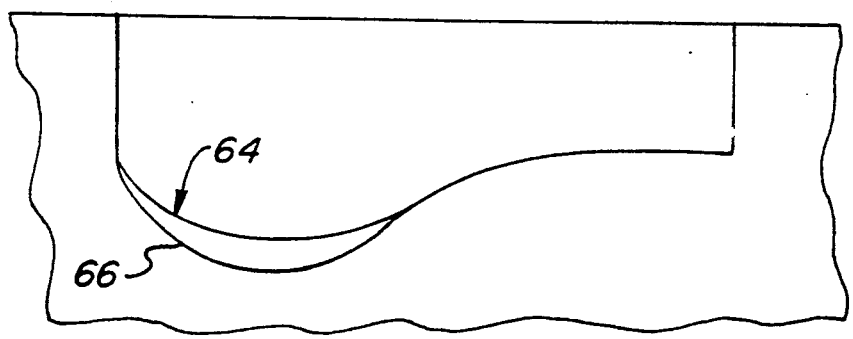
FIG. 11 is a vertical cross-sectional view of the surgical stapling device anvil shown in FIGS. 9 and 10, and taken on arcuate surface A—A in FIG. 10.

One type of anvil 52 used to deform the polymeric staple in accordance with the present invention is shown in FIGS. 9 through 11. Anvil 52 has a supporting structure 54 having a staple-receiving face 56. The face and supporting structure can be either a one or multi-piece construction.

The face 56 includes two guiding paths 58 for receiving and guiding or steering the staple legs to the desired configuration.

It will be appreciated that while the anvil shown in FIGS. 9 through 11 includes but one pair of guiding paths 58, in the usual case an elongated row of pairs of such pockets would be formed in a similarly elongated support structure 54 so that a large number of surgical staples can be driven simultaneously or in rapid sequence.

Guiding paths 58 curve from respective entry ends 60 to exit ends 62. The guiding paths curve relative to the horizontal plane y-z as shown in FIG. 10 to bend the curved second portions of the legs as described above. As shown in FIG. 11, the guiding paths 58 include a sunken pocket 64 for receiving the end points and forming the bend in each staple leg. The sunken pockets include a relief channel 66 having a width less than that of the legs. In this manner, when the legs enter the sunken pockets the end points will extend into the relief channel but will not reach its bottom surface. This protects the chiseled end points from breaking off. The guiding paths 58 slope upwardly from the sunken pockets to guide the legs toward the back span, while at the same time the horizontal curves of the guiding paths cross over each other and extend past the entry ends of the opposite guiding path so the legs are deformed into the pretzel shape as described above.

The anvil is arranged in the surgical stapling device so that longitudinal axis B—B (see FIG. 10) is substantially parallel to the back span of a staple to be driven toward the anvil. Moreover, the entry ends 60 of the respective paths 58 are spaced so as to receive the respective end points 36 of the legs 34 of the staple driven toward the anvil. Accordingly, when the staple is so driven, the end points 36 each first encounter the entry end 60 of one guide path 58. As driving of the staple toward the anvil continues, the end points 36 are steered along the curved guide paths 58 to form a knot in the legs and the end points are ultimately driven within the gap formed between the underside of the back span and the bend of the opposite leg when driving is completed.

Thus it can be seen that the surgical stapling device anvil in accordance with the present invention will cause a malleable staple driven theretoward to assume a unique desired deformed configuration. Moreover, since this anvil is specifically designed to be used with malleable, bioabsorbable staples, which are made of polymeric material, it need not itself be made of a hardened material like metal. This factor is important because precisely shaped anvil pockets such as described above are difficult to form in hardened metal by other than very expensive machining techniques. Indeed coining or punching techniques for forming anvil pockets of conventional shape in known metal anvils are not suitable for forming the precisely shaped anvil pockets in accordance with the present invention. Thus plastics can be used to make the inventive anvil using precise yet inexpensive injection molding methods in the production process. Still further, plastics from which the anvil of the present invention may be made are themselves less expensive than metals used in conventional anvils. Therefore, the present invention provides significant advances over the prior art.

It has been found that polymeric materials like polycarbonate and liquid crystal polymer (LCP) may suitably be used for the inventive anvil.

As will be readily appreciated by those skilled in the art, the present invention provides marked improvements over known surgical staples and stapling device anvils. It achieves all of the benefits of known bioabsorbable, polymeric staples without the associated drawbacks. Moreover, by taking advantage of the unique properties of recently developed malleable, bioabsorbable, polymeric staples, this invention provides a unique deformed staple shape, as well as a unique surgical stapling device anvil structure and method for producing that shape.

Although specific embodiments of the present invention have been described above in detail, it will be understood that this description is merely for purposes of illustration. Various modifications of and equivalent structures corresponding to the disclosed aspects of the preferred embodiment in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A deformed malleable, bioabsorbable polymeric surgical staple, comprising:
   a back span; and
   first and second legs extending in a first direction from opposite ends of said back span, each of said first and second legs terminating in an end point, wherein
   each leg includes a bend and a curved portion extending across a vertical plane, with the vertical plane extending in the first direction and through said back span, and with the curved portions of each respective leg crossing with each other.

2. A deformed malleable, bioabsorbable polymeric surgical staple according to claim 1, wherein each said end point extends between said bend in an opposite leg and an underside of said back span.

3. A deformed malleable, bioabsorbable polymeric surgical staple according to claim 2, wherein each said leg comprises a straight portion between said bend and said back span, with said straight portion extending substantially perpendicularly from said back span.

4. A deformed malleable, bioabsorbable polymeric surgical staple according to claim 3, wherein said curved portion extends from said bend at a distal end of said leg, said curved portion being arcuately shaped and extending toward an opposite leg and upwardly toward said back span.

* * * * *